| United States Patent [19] | [11] | 4,018,854 |
|---|---|---|
| McIntosh | [45] | Apr. 19, 1977 |

[54] CARBOXYPHOSPHONATES

[75] Inventor: Colin Leslie McIntosh, Newark, Del.

[73] Assignee: E. I. Du Pont de Nemours and Company, Wilmington, Del.

[22] Filed: June 25, 1975

[21] Appl. No.: 590,374

Related U.S. Application Data

[60] Division of Ser. No. 474,537, May 30, 1974, abandoned, which is a continuation-in-part of Ser. No. 381,619, July 23, 1973, abandoned.

[52] U.S. Cl. .................................. 260/941; 71/86
[51] Int. Cl.$^2$ .................... C07C 9/32; A01N 9/36

[58] Field of Search .................................. 260/941

[56] References Cited

UNITED STATES PATENTS 3,943,201  3/1976  McIntosh ........................ 260/941

*Primary Examiner*—Anton H. Sutto

[57] ABSTRACT

Carboxyphosphonates such as trisodium carboxyphosphonate are useful for regulation of plant growth.

2 Claims, No Drawings

CARBOXYPHOSPHONATES

RELATED APPLICATIONS

This is a division of application Ser. No. 474,537, filed May 30, 1974, which is a continuation-in-part of application Ser. No. 381,619 filed July 23, 1973, both now abandoned.

BACKGROUND OF THE INVENTION

This invention relates to carboxyphosphonates and their use as brush control agents. The use of various carbamoylphosphonates for control of plant growth is known in the art. For example, U.S. Pat. No. 3,627,507 and Offenlegungsschrift 2,040,367 relate to the use of carbamoylphosphonates for plant growth control. However, neither of these references suggest the carboxyphosphonates of this invention. Berichte 57, 1023 (1924) describes trisodium carboxyphosphonate as well as the zinc, manganese, copper, lead and silver salts. However, this reference does not describe any utility for these salts.

SUMMARY OF THE INVENTION

Plant growth can be regulated by application to the plants of compounds of the formula

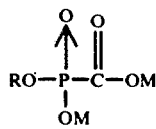

wherein
M is selected from sodium, lithium, potassium calcium, magnesium, zinc, manganese, barium or

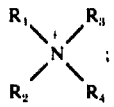

R is M, alkyl of 1 to 8 carbons, optionally substituted with a chlorine, a bromine, a fluorine, or an iodine atom; alkenyl of 3 to 8 carbon atoms,

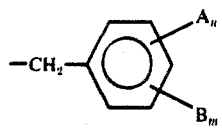

where
A is chlorine or methyl, B is chlorine or methyl, $n$ is 0 or 1, and $m$ is 0 or 1;
$R_1$ is hydrogen, alkyl of 1 to 4 carbon atoms, or hydroxyalkyl of 2 to 4 carbon atoms;
$R_2$ is hydrogen, alkyl of 1 to 4 carbon atoms, or hydroxyalkyl of 2 to 4 carbon atoms;
$R_3$ is hydrogen, alkyl of 1 to 4 carbon atoms, or hydroxyalkyl of 2 to 4 carbon atoms; and
$R_4$ is hydrogen or alkyl of 1 to 12 carbon atoms, provided that the total number of carbon atoms in $R_1$, $R_2$, $R_3$ and $R_4$ is less than 16.

Of these compounds, those wherein R is alkyl of 1 to 4 carbon atoms or M where M is sodium or potassium are preferred. Within this group preferred compounds are trisodium carboxyphosphonate, disodium ethyl carboxyphosphonate, and disodium methyl carboxyphosphonate.

The active compounds described above can be applied to plants to regulate plant growth. The phrase "applied to plants" as used herein includes both direct application to the plants and also application to the soil in which the plants grow.

Of the compounds described above, those where M is limited to lithium, potassium, calcium, magnesium, barium or

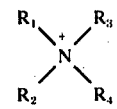

and R is M or alkyl of 1 to 8 carbon atoms, optionally substituted with a chlorine, bromine, fluorine or iodine atom; alkenyl of 3 to 8 atoms; or

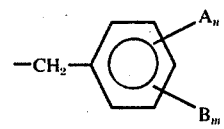

where A is chlorine or methyl and B is chlorine or methyl; $n$ is 0 or 1; $m$ is 0 or 1, are novel.

DESCRIPTION OF THE PREFERRED EMBODIMENTS

The compounds useful in this invention are formed by alkaline hydrolysis of the appropriately substituted alkyl carboxyphosphonate. The hydrolysis is conducted by refluxing the starting material in aqueous solutions having 2 or 3 equivalents of alkali metal hydroxide. Once an alkali metal salt is formed, other salts can be formed by reaction with metal salts of other acids or by conventional ion exchange. It should be noted that the activity of the compounds useful in this invention resides in the carboxyphosphonate anion. The exact identity of the cations with which it is associated is of little significance. The preparation of the compounds of this invention is further illustrated by the following examples.

EXAMPLE 1

Using the method of Nylen, Ber., 57B, 1023 (1924), a solution of 21 parts of triethyl carboxyphosphonate in 60 parts of water containing 24 parts of 50% sodium hydroxide was refluxed for 2 hrs. The solution was allowed to cool overnight. Filtration of the reaction mixture gave 4.7 parts of the product, trisodium carboxyphosphonate hexahydrate, mp >250°; $\nu_{KBr}$ = 1560, 1530 cm$^{-1}$.

In a similar manner, by using the appropriate metal hydroxide, the following compounds can be prepared:

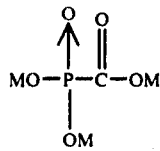

(R is M)

M

Li
K
Ca
Mg
Zn
Mn
Ba

The triammonium salts cannot be prepared directly by hydrolysis of the trialkyl esters. They must be obtained by passage of a solution containing trisodium carboxyphosphonate through an ion exchange column previously treated with the appropriate ammonium cation.

In such a manner, the following compounds can be prepared

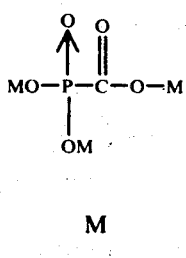

M $NH_4$
$(CH_3)NH_3$
$(C_4H_9)NH_3$
$(C_{12}H_{25})NH_3$
$(CH_3)_2NH_2$
$(CH_3)NH_2(C_{12}H_{25})$
$(CH_3)_3NH$
$(C_4H_9)_3NH$
$(CH_3)_4N$
$(CH_3)_3N(C_4H_9)$
$(CH_3)_3N(C_{12}H_{25})$
$(C_2H_4OH)NH_3$
$(HOCH_2CH_2CH_2CH_2)NH_3$
$(CH_3)NH_2(CH_2CH_2OH)$
$(CH_3)N(CH_2CH_2OH)_3$

EXAMPLE 2

A solution of 15.5 parts of ammonium ethyl carbamoylphosphonate and 16 parts of 50% sodium hydroxide in 50 parts of water was refluxed for 2 hours. The solution was cooled and evaporated under vacuum to dryness to give the disodium ethyl carboxyphosphonate, m.p. >300°, $\nu_{neat}$ = 1580 (C=O), 1080 (P—O$^-$), 1040 (P—OCH$_2$CH$_3$) cm$^{-1}$.

EXAMPLE 3

To a solution of 8.5 parts of trimethyl carboxyphosphonate in 50 parts of water was added slowly 8.0 parts of 50% sodium hyroxide. The solution was refluxed for 1 hour, cooled and the solvent removed under vacuum to give 10.6 parts of disodium methyl carboxyphosphonate, m.p. >250°, $\nu_{neat}$ = 1580, 1080 (P—O$^-$), 1050 (P—OCH$_3$)cm$^{-1}$.

In a similar manner, by using the appropriate metal hydroxide and phosphonate ester, the following compounds can be prepared:

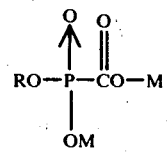

| R | M | m.p. | $\nu$ Neat (P—O$^-$) |
|---|---|---|---|
| CH$_2$=CHCH$_2$ | Na | >300° | 1100 cm$^{-1}$ |
| CH$_3$CH$_2$CH$_2$CH$_2$ | Na | >300° | 1105 cm$^{-1}$ |
| C$_6$H$_5$CH$_2$ | Na | >300° | 1100 cm$^{-1}$ |
| CH$_3$CH$_2$CH$_2$CH$_2$CH$_2$CH$_2$ | Na | — | |
| CH$_3$CH$_2$CH$_2$CH$_2$CH$_2$CH$_2$ | K | — | |
| CH$_2$=CHCH$_2$ | Li | — | |
| CH$_2$=CHCH=<br>          \|<br>          CH$_3$ | Ca | — | |
| ClCH$_2$CH$_2$ | Mg | — | |
| CH$_3$CH$_2$CH$_2$CH$_2$CHCH$_2$<br>                      \|<br>                      CH$_2$<br>                      \|<br>                      CH$_3$ | Zn | — | |
| CH$_2$=CHCH$_2$CH$_2$ | Mn | — | |
| CH$_3$CH$_2$CH$_2$CH$_2$ | Ba | — | |
| BrCH$_2$CH$_2$— | Na | | |
| FCH$_2$CH$_2$— | Na | | |
| ICH$_2$CH$_2$— | Na | | |
| CH$_3$—⟨C$_6$H$_4$⟩—CH$_2$— | Na | | |
| Cl—⟨C$_6$H$_4$⟩—CH$_2$— | Na | | |

-continued

| R | M | m.p. | ν Neat (P—O) |
|---|---|------|--------------|
| 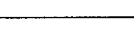 | K | | |
| $CH_3CH_2CH_2CH_2CH_2-CH=CH-CH_2-$ | Na | | |

By passage of a solution of an appropriate disodium alkyl carboxyphosphonate through an appropriate ion exchange column, pretreated with the appropriate ammonium cation, the following compounds can be prepared:

$$R-O-\overset{\overset{O}{\uparrow}}{\underset{\underset{OM}{|}}{P}}-\overset{O}{\overset{\|}{C}}OM$$

| R | M |
|---|---|
| $CH_3$ | $NH_4$ |
| $CH_3CH_2-$ | $NH_4$ |
| $CH_3CH_2CH_2CH_2$ | $(CH_3)NH_3$ |
| $CH_2=CHCH_2$ | $(C_4H_9)NH_3$ |
| $CH_3CH_2$ | $(C_{12}H_{25})NH_3$ |
| 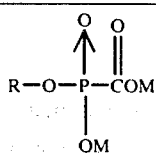 | $(CH_3)_2NH_2$ |
| $ClCH_2CH_2$ | $(CH_3)NH_2(CH_2CH_2OH)$ |
| $CH_2=CCH_2$<br>$\|$<br>$CH_3$ | $(C_4H_9)_2NH_2$ |
| $CH_3$ | $(CH_3)_3NH$ |
| $CH_3CH_2CH_2CH_2$ | $(C_4H_9)_3NH$ |
| $CH_3CH_2$ | $(HOCH_2CH_2CH_2CH_2)_3NH$ |
| $CH_3CH_2$ | $(CH_3)_4N$ |
| $CH_2=CHCH_2CH_2$ | $(CH_3)_3N(C_{12}H_{25})$ |
| $CH_3CH_2CH_2CH_2CH_3CH_2CH_2$ | $NH_4$ |
| $CH_3CH_2CH_2CH_2CH_2CH_2CH_2CH_2$ | $(CH_3)NH_3$ |

The compounds of this invention are useful for controlling the growth of plants. The compounds of this invention are particularly useful for preventing bud break and retarding the growth of woody plants. Thus, the compounds of this invention can be applied in areas such as power line rights-of-way where low-growing and slow-growing vegetation is especially desirable.

In addition to their value as plant growth retardants, the compounds of this invention can also be used to control flowering, fruit set, and coloration on apples and other fruits. They are useful in controlling the growth and flowering of ornamental species such as chrysanthemum and azalea.

The compounds of this invention can also be used to prolong the dormancy of perennial plants, and thereby protect the upsprouted buds from frost damage. This can be especially important in the protection of flower buds, which in some years may sprout early and be killed by cold temperatures. Application to plants in the stage where the next year's buds are being initiated, or are developing gives marked retardation of bud break the following spring and greatly reduced growth.

To illustrate the growth-retardant activity of the compounds of this case, the following data are presented.

In one test, the test compound was applied in a solvent with a wetting agent with a humectant to cotton plants (five-leaf stage including cotyledons), brush bean (second trifoliate leaf expanding), morningglory (four-leaf stage including cotyledons), cocklebur (*Xanthium* sp., four-leaf stage including cotyledons), *Cassia tora* (three leaves including cotyledons), nutsedge (*Cyperus rotundus*, three to five-leaf stage). crabgrass (*Digitaria* sp., two-leaf stage), barnyardgrass (*Echinochloa* sp., two-leaf stage), wild oats (*Avena fatua*, one-leaf stage), wheat (two-leaf stage), corn (three-leaf stage), soybean (two cotyledons), rice (two-leaf stage), and sorghum (three-leaf stage).

Treated plants and controls were maintained in a greenhouse for 16 days, than all species were compared with controls end visually rated for response to treatment.

POST EMERGENCE

| COMPOUND | Kg/Ha | Bush Bean | Cotton | Morning Glory | Cockle bur | Cassia | Nut sedge | Crab grass | Barnyard Grass | Wild Oats | Wheat | Corn | Soybean | Rice | Sorghum |
|---|---|---|---|---|---|---|---|---|---|---|---|---|---|---|---|
| $H_3COPCOH$ (OO‖‖‖) OH 2 Na⁺ | 2 | 2C 10P | 9G 2H | 7C | 6G 2C | 7C | 0 | 0 | 7G 3C | 0 | 0 | 7G 5U | 9P 5I | 0 | 7G 3U |
| $CH_3CH_2OPCOH$ (OO‖‖‖) OH 2 Na⁺ | 2 | 8G 8Q 2H | 8G 2H | 8G | 0 | 0 | 0 | 0 | 0 | 0 | 0 | 5G 1U | 0 | 2G | 7G 2U |

-continued

POST EMERGENCE

| COMPOUND | Kg/Ha | Bush Bean | Cotton | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|---|---|
| $CH_2=CHCH_2O\overset{\overset{O}{\|}}{P}\overset{\overset{O}{\|}}{C}OH$ <br> $\|$ <br> $OH$ <br> $2\ Na^+$ | 2 | 9C 9D | 9G 3C | 7C | 2G | 5G | 0 | 6G | 8G 3C | 6G 2C | 6G 1C | 7G 1C | 10P | 1C | 7G 1C |
| $C_4H_9O\overset{\overset{O}{\|}}{P}\overset{\overset{O}{\|}}{C}OH$ <br> $\|$ <br> $OH$ <br> $2\ Na^+$ | 2 | 9D 7C | 6G 1C | 8C | 2G | 5G | 0 | 5G | 8C | 3G | 5G | 7G 1C | 6G | 5G | 7G |
| $\bigcirc\!\!-\!CH_2O\overset{\overset{O}{\|}}{P}\overset{\overset{O}{\|}}{C}OH$ <br> $\|$ <br> $OH$ <br> $2\ Na^+$ | 2 | 9G 6Y | 5G | 4G | 2G | 0 | 0 | 2G | 2C 7G | 2G | 2G | 1C 7G | 9P | 6G | 7G |

In another test, the test compound was applied in a similar solvent to pots of privet (*Ligustrum* sp.), willow (*Salix* sp.), forsythia (*Forsythia* sp.), Arbor Vitae (*Thuja* sp.), and apple (*Malus* sp.). The plants were maintained in a greenhouse. Plant response ratings were taken 1 week and 4 weeks after application.

| Compound | Application Rate Kg./hectare | Privet 1 wk | Privet 4 wks | Willow 1 wk | Willow 4 wks | Forsythia 1 wk | Forsythia 4 wks | Arbor Vitae 1 wk | Arbor Vitae 4 wks | apple 1 wk | apple 4 wks |
|---|---|---|---|---|---|---|---|---|---|---|---|
| $HO\!-\!\overset{\overset{O}{\|}}{P}\!-\!\overset{\overset{O}{\|}}{C}\!-\!OH$ <br> $\|$ <br> $OH$ <br> $3\ Na^+$ | 2.2 <br> 0.6 | 0 <br> 0 | 5G <br> 0 | 0 <br> 0 | 8G5X <br> 5X | 0 <br> 0 | 10G <br> 10G | 0 <br> 0 | 0 <br> 0 | 0 <br> 0 | 6G <br> 0 |

In a third test, the test compounds was applied in a similar solvent to pots of Black Valentine bean (*Phaseolus vulgaris* cv. Black Valentine), apple (*Malus* sp.) *and willow* (*Salix* sp.). The plants were maintained in a greenhouse, and plant response ratings were taken after application as indicated.

| IN NO. | Rate Kg/Ha | B.V. Bean 1 week | B.V. Bean 4 weeks | Apple 1 week | Apple 4 weeks | Willow 1 week | Willow 4 weeks |
|---|---|---|---|---|---|---|---|
| $H_3CO\overset{\overset{O}{\|}}{P}CO\ Na^+$ <br> $\|$ <br> $O$ <br> $Na^+$ | 1 <br> 4 | 9G <br> 9G | 10C <br> 10C | 0 <br> 0 | 6G <br> 3X 10G | 7G <br> 10G | 6G5X <br> 9G5X |

The plant response ratings (above) are composed of a number and a letter. The number describes the extent of the response and ranges from zero to 10 with zero representing no response, and ten representing 100% response. The letter describes the type of the response, as follows:

C, chlorosis-necrosis
D, defoliation
H, formative effect (Malformation)
U, unusual pigmentation
G, growth retarded
P, terminal bud injury
X, axillary stimulation
I, increased chlorophyll
8Q*, increased fruit size
8Y*, Abscised buds or flowers

*Note: With the "8Q" and "6Y", the number does not refer to extent of response (any percent increase in fruit size is represented by an 8Q).

The term "plant growth retardant" as used in this disclosure is to be understood to mean an agent which, when applied to a plant or its environs, will slow the growth of the plant. This also includes a delaying response on bud sprouting or prolonging of the dormancy period.

The compounds of this invention can be applied as foliar sprays or as soil applications to retard the growth rate of such plants or to affect flowering and fruit set.

Preferably, the compounds of this invention are applied as foliar or dormant wood sprays to the point of runoff although lower-volume application can also be effective.

The compounds of the invention are very versatile and may be applied at one of many different time periods to suit the convenience of the applicator. For example they may be applied in Spring a short time prior to the period when maximum plant growth is anticipated, to effect growth retardation. They may be applied later in the growing season just after trimming, to effect growth retardation. Or they may be applied when the year's growth has ceased (late Summer, Fall, or Winter) with the result that treated plants will remain dormant the following Spring, whereas untreated plants will sprout and grow. If flowering and fruit set are to be modified, the treatment is applied before, during, or shortly after flowering.

It will be recognized that the application rate is dependent upon the species to be treated and the results desired. In general, rates of from 0.25 to 20 kilograms per hectare are used although higher or lower rates can achieve the desired effect in some instances.

Useful formulations of the compounds of this invention can be prepared inconventional ways. They include dusts, granules, pellets, solutions, suspensions, emulsions, wetting powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1 to 99% by weight of active ingredient(s) and at least one of (a) about 0.1 to 20% surfactant(s) and (b) about 5 to 99% solid or liquid diluent(s). More specifically, they will contain these ingredients in the following approximate proportions.

|  | Active Ingredient | Percent by Weight Diluent(s) | Surfactant(s) |
| --- | --- | --- | --- |
| Wettable Powders | 20-90 | 0-74 | 1-10 |
| Oil Suspensions and Emulsions | 5-50 | 40-95 | 0-15 |
| Aqueous Solutions | 10-50 | 50-90 | 0-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing. Likewise, high levels of oils or humectants can be incorporated either in the formulation or by tank-mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending, and, usually grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th. Edn., McGraw-Hill, N.Y. 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

W. P. Langsdorf, U.S. Pat. No. 3,627,507, Dec. 14, 1971. col. 8, line 1 through col. 11, line 12 and Examples 60-65.

B. C. Klingman, "Weed Control as a Science", John Wiley & Sons, Inc., New York, 1961 pp. 81-96.

J. D. Fryer and S. A. Evans, "Weed Control Handbook", 5th Edn. Blackwell Scientific Publications, Oxford, 1968, pp. 101-103.

The following Examples further illustrate the formulation and application of the compounds of this invention.

EXAMPLE 4

| Wettable Powder | |
| --- | --- |
| disodium methyl carboxyphosphonate | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of this invention may be formulated in the same manner.

Fifteen kilograms of this formulation are mixed with 600 liters of water in a sprayer fitted with an agitator. The mixture is sprayed on a one hectare area of newly trimmed hedgerow in the spring after the leaves have expanded. (The spray may be either directly on the plants or to the locus of the plants.) This treatment greatly reduces the growth of plants growing in the hedgerow, but does not seriously injure them. Thus, the hedgerow is kept neat with a minimum of labor expended for trimming it.

EXAMPLE 5

| Water-Soluble Powder | |
| --- | --- |
| disodium ethyl carboxyphosphonate | 95.0% |
| dioctyl sodium sulfosuccinate | 0.5% |

-continued

Water-Soluble Powder

| | |
|---|---|
| sodium ligninsulfonate | 1.0% |
| synthetic fine silica | 3.5% |

The ingredients are blended and coarsely ground in a hammer mill so that only a few percent of the active exceeds 250 microns (U.S.S. No. 60 sieve) in size. When added to water with stirring, the coarse powder initially disperses and then the active ingredient dissolves so that no further stirring is needed during application.

Ten kilograms of this formulation are dissolved in 800 liters of water containing 0.5% of a non-phytotoxic wetting agent. This formulation is sprayed from a helicopter to a one hectare area under an electric power line in which the brush and trees have been freshly trimmed. This treatment retards the growth of black willow (*Salix nigra*), black cherry (*Prunum serotina*), and many other woody species.

EXAMPLE 6

Solution

| | |
|---|---|
| trisodium carboxyphosphonate | 12.5% |
| octylphenoxypolyethoxyethanol | 0.5% |
| water | 87.5% |

The ingredients are combined and stirred to produce a solution which can be applied directly or after dilution with additional water.

Fifteen liters of this solution are mixed with 200 liters of water and sprayed in late summer on a one hectare area of woody plants growing on a power line right-of-way. The treated plants continue to appear like untreated plants. However, the following year the treated plants remain dormant for an extremely long period of time, whereas untreated ones sprout and grow normally. Thus, the treatment greatly reduces the amount of labor required to maintain the plants at a desirable height.

EXAMPLE 7

Oil Suspension

| | |
|---|---|
| trisodium carboxyphosphonate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

One part of this suspension is mixed with one part of water in a sprayer fitted with an agitator, and applied in winter to the point of runoff on the bark of dormant woody plants growing under a power line. The treated plants remain dormant for an extremely long period of time, thus greatly reducing plant growth and also the labor required for pruning.

I claim:

1. A compound of the formula:

$$\text{RO}-\overset{\overset{\displaystyle O}{\uparrow}}{\underset{\underset{\displaystyle OM}{|}}{P}}-\overset{\overset{\displaystyle O}{\|}}{C}-\text{OM}$$

wherein
M is sodium, lithium, potassium, calcium, magnesium, or barium
R is alkyl of 1 to 8 carbons, optionally substituted with a chlorine, a bromine, a fluorine, or an iodine atom; alkenyl of 3 to 8 carbon atoms, or $$-CH_2-\underset{B_{[n]m}}{\overset{A_n}{\bigcirc}}$$

where
A is chlorine or methyl,
B is chlorine or methyl,
n is 0 or 1,
m is 0 or 1.

2. The compound of claim 1, disodium methyl carboxyphosphonate.

* * * * *